United States Patent
Horstmann et al.

[11] Patent Number: 6,074,665
[45] Date of Patent: Jun. 13, 2000

[54] TRANSDERMAL THERAPEUTIC SYSTEM FOR ADMINISTERING ACTIVE AGENTS TO THE HUMAN BODY VIA THE SKIN

[75] Inventors: Michael Horstmann, Neuwied; Johannes Leonhard, Bendorf; Walter Müller, Neuwied, all of Germany

[73] Assignee: LTS Lohmann Therapie-Systeme GmbH, Neuwied, Germany

[21] Appl. No.: 08/983,643

[22] PCT Filed: Jun. 24, 1996

[86] PCT No.: PCT/EP96/02735

§ 371 Date: Jan. 28, 1998

§ 102(e) Date: Jan. 28, 1998

[87] PCT Pub. No.: WO97/04818

PCT Pub. Date: Feb. 13, 1997

[30] Foreign Application Priority Data

Jul. 29, 1995 [DE] Germany ............ 195 27 925

[51] Int. Cl.[7] ............................... A61F 13/02
[52] U.S. Cl. .............................. 424/449; 424/448
[58] Field of Search ........................ 424/448, 449

[56] References Cited

U.S. PATENT DOCUMENTS 3,797,494  3/1974  Zaffaronti .
5,071,704  12/1991  Fischel-Ghodsian .
5,676,968  10/1997  Lipp ................................. 424/448

FOREIGN PATENT DOCUMENTS 2 397 190  2/1979  France .
1 414 812  11/1975  United Kingdom .

OTHER PUBLICATIONS

T. Higuchi, "Physical Chemical Analysis of Percutaneous Absorption Process from Creams and Ointments", Journal of the Society of Cosmetic Chemists, pp. 85–97, 1959.

T. Kokubo et al., "Diffusion of Drugs in Acrylic–Type Pressure–Sensitive Adhesive Matrices", Proceedings of the International Symposium on Controlled Release Bioactive Materials, 17, pp. 270–272, 1990.

K. Sugibayashi et al. "Polymers for Transdermal Drug Delivery Systems", J. Controlled Release, vol. 29, No. 2, Feb. 1994.

*Primary Examiner*—Carlos Azpuru
*Attorney, Agent, or Firm*—Wenderoth, Lind & Ponack, L.L.P.

[57] ABSTRACT

A transdermal therapeutic system having a layered structure, comprising a backing layer (1) and at least one active substance-containing matrix layer (2), for storage purposes being placed onto a removable protective layer (4) coated with an abherent (3) is characterized in that said abherent (3) has a lower diffusion coefficient for the active substance used than the base materials used in the matrix layer (2) or in the matrix layers.

8 Claims, 1 Drawing Sheet

TRANSDERMAL THERAPEUTIC SYSTEM FOR ADMINISTERING ACTIVE AGENTS TO THE HUMAN BODY VIA THE SKIN

This application is a 371 continuation of PCT/EP 96/02735 filed Jun. 24, 1996, which is continuation of DE/9527925.5 filed Jul. 29, 1995.

BACKGROUND OF THE INVENTION

1. Field of the Invention

The invention relates to a transdermal therapeutic system for delivering active substances to the human body via the skin.

2. Description of the Relted Art

Transdermal therapeutic systems (TTS) have already been introduced on the market for the therapeutic therapy of a number of illnesses.

A disadvantage of the systems according to the prior art is the insufficient skin permeability of many active substances, which permeability cannot be improved above a certain limit, the so-called "saturation flow", even through numerous galenic measures taken in respect of the TTS design (use of multi-layered systems, use of control membranes, variation of the active substance concentration, modification of the base polymers, etc.). The statement that the transdermal flow of an active substance from the solid, finely dispersed phase can in principle not be increased any further, even despite the use of more strongly dissolving vehicles, can already be found in the works of Higuchi, which are pathbreaking to this day (e.g. T. Higuchi: Physical Chemical Analysis of percutaneous absorptions process from creams and ointments. J. Soc. Cosmetic Chem, 11, S. 85–97 (1960).

With a great number of active substances, however, there is the possibility of adding a penetration enhancer, a so-called "enhancer", to the TTS during its manufacture. Generally, these are liquid or volatile additives improving the absorption properties of the human skin, thus enabling a sufficiently high absorption of the active substance from a relatively small TTS area. However, highly volatile enhancers, such as, for example, ethanol, which is used for the active substance estradiol, present problems due to the strong softening of the adhesive layers of the TTS, thus necessitating further space-consuming compartments in the system, which renders the TTS unacceptably thick or its surface area unacceptably large. Moreover, each additional non-polymeric additive involves a risk of incompatibility reactions on the skin, possibly also of sensitisation. Through adding certain less volatile, but mostly also less active, enhancers (e.g. glycerol esters, cyclic amides, eucalyptol) it is possible to prepare matrix systems which contain the active substance and the absorption-enhancing components in one or more monolithic layers. According to the prior art it is, however, not possible to achieve a satisfactory therapy with such TTS if the enhancers have poor skin compatibility or if the systems, due to the flux through the skin being still too low, require unacceptably large surface areas.

Another possibility of increasing the active substance flow through the skin is to dissolve a greater amount of the active substance in a molecular-disperse manner than corresponds to the saturation solubility. With such oversaturation of these systems, the rate of permeation through the skin increases to the same extent. Since such states are thermodynamically unstable, it is difficult to provide such administration forms in a form which can be stored; a recrystallisation process of active substance particles takes place whose onset and duration cannot be foreseen. This recrystallisation process results in the flow rate through the skin gradually falling to the saturation flow level, thus causing a loss of a large part of the initially present therapeutic activity, depending on the initial concentration.

In a great number of cases where such recrystallisation occurred it was observed that crystallisations have their origin not in the components of the TTS but in the abherent layer.

SUMMARY OF THE INVENTION

Starting from the above-mentioned prior art it is the object of the invention to provide a transdermal therapeutic system which has a layered structure comprising a backing layer and at least one active substance-containing matrix layer and which is not subject to premature precipitation, or only to inconsiderable premature precipitation, of the active substance when stored in contact with a removable protective layer which is pre-coated with an abherent.

According to the invention this object is achieved in that the abherent has a lower diffusion coefficient for the active substance used than the base materials used in the matrix layer or in the matrix layers. This is achieved, in particular, by using fluorine-containing polymers as components of the abherent layer.

DESCRIPTION OF THE PREFERRED EMBODIMENTS

Figure 1:
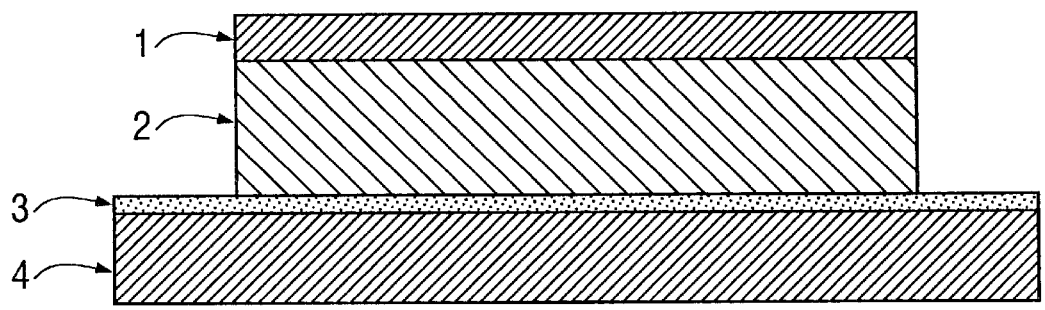
FIG. 1 illustrates, by way of example, a system according to the invention, comprising backing layer (1), matrix (2), abherent (abherent layer) (3) and protective layer (4). Matrix (2) can also be multi-layered.

By means of series of investigations with different pairings between single-layered and multilayered matrices as well as with protective layers coated with different abherents, it was surprisingly found that recrystallisation processes regularly slow down or even do not occur at all if abherents are selected which have a low diffusion coefficient.

Thus, in the sense of the invention, fluorine-containing polymers are found particularly suitable, which, besides the more common silicone-based abherents, are available on the market in sufficient quality. A great variety of such abherents is already available in prefabricated composites with the protective sheet, the latter generally having a greater thickness. The use of abherent-coated foils or sheets is preferable to the use of full layers of the abherent because it results in a reduction of the costs for the, frequently expensive, abherent, or because advantages with regard to strength are achieved. However, in accordance with the invention, it is also possible to provide the protective layer including the abherent layer from one uniform material.

The particularly preferred fluorocarbon polymers may consist of polytetrafluoroethylene, perfluoroethylenepropylene copolymers, perfluoroalkoxy copolymers, polychlorotrifluoroethylene, ethylene-tetrafluoroethylene copolymers, ethylene-chlorotrifluoroethylene copolymers, polyvinylidene fluoride or even polyvinyl fluoride, this enumeration not being exhaustive but merely serving to illustrate a selection of possibilities.

Furthermore, the abherents may also consist of other substances that are poorly diffusible in comparison with the matrix base material, such as, for instance, polyethylene, polypropylene, polyvinylchloride or polyvinylidene chloride, provided they have sufficient parting properties.

Apart from the common acrylic-acid ester copolymers other polymers may be used as base material, such as polyisobutylene, polyvinylacetate and copolymers, synthetic rubber, and silicones. If required, for example for achieving sufficient adhesive power, mixtures of such and other polymers with additives, e.g. resins, skin-compatible oil components, fillers, etc., may be used, the base materials of the matrix layer or matrix layers consisting for the most part of water-insoluble skin-compatible polymers and of resin components suitable for skin contact.

The effect according to the invention is, however, most apparent if copolymers of dienes and styrene, polyisobutylene or natural rubber are used, and derivatives of natural resins or hydrocarbon resins are added as tackifiers.

The advantage of the invention can be observed particularly with active substances which are solid at the intended storage temperature. Of these, the following are to be mentioned in particular:

Centrally active substances such as, for example, amantadine, benztropine, biperiden, bornaprine, trihexyphenidyl, tranylcypromine, physostigmine, selegilin, doxepin, maprotiline, imipramine, perphenazine, haloperidol, benperidol, sulpiride, pimozide, methylphenidate, amphetamimil, amphetamine, cocaine, oxazepam, alprazolam, diazepam, lorazepam, buspirone, xanomeline, piracetam, ephedrine, norpseudoephedrine, fenproporex, fenfluramine, Opioid analgesics such as morphine, heroine, tilidine, alfentanile, methadone, sufentanil, fentanyl, Peripherally active analgesics such as ketorolac, ketoprofene, indomethacin, acetylsalicylic acid, diclofenac, tenoxicam, Anticoagulants such as warfarin, phenprocoumone, acetylsalicylic acid, acenocoumarol, Antihistaminics such as pheniramine, chlorpheniramine, terfenadine, trimetindene, prednisolone, bamipine, clemastin, Steroid hormones, for example for post-menopausal, anabolic, contraceptive or anti-inflammatory use, such as medroxyprogesterone, levonorgestrel, testosterone, methenolone, nandrolone, androsterone, cyproterone acetate, medroxyprogesterone acetate, lynoestrenol, norethisterone, epimestrol, estriol, estrone, estradiol valerate, estradiol propionate, norethisterone acetate, norgestrel, gestodene, mestranol, estradiol, ethinylestradiol, Prostaglandins, such as gemeprost, dinoprostone, sulproston, Osteoprotective substances such as vitamine D3, raloxifene, etidronic acid, Hypotensive substances such as enalapril, captopril, moxonidine, clonidine, timolol, propanolol, bupranolol, bopindolol, metoprolol, pindolol, mepindolol, Sympathotonic substances such as etilefrine, ephedrine, midodrine, Antiallergics such as phenuramine, brompheniramine, ketotifen, terfenadine, dimethindene maleate, cyproheptadine, local anaesthetics such as salbutamol, clenbuterol, tulobuterol, atropine scopolomine, fenoterol, and many other active substances which are not mentioned here in detail.

According to the invention, the diffusibility of the abherent is to be lower than that of the base material of the matrix layers. In the literature a number of methods for determining the diffusion coefficient are described which are derived from Fick's laws. Thus, it is, for example, possible to examine layers of the abherent or of a matrix base material which are preloaded with active substance, at a determined temperature in a diffusion cell, in which the released substance amount can be determined in dependence on time. The process of determining the diffusion coefficient can be carried out, for example, according to Kokubo et al., Proceed. Intern. Symp. Control, Rel. Bioact. Mater. 17 (1990), pages 271–272. In the TTS according to the invention, the resulting diffusion coefficient of the abherent is to be smaller than the diffusion coefficient of the matrix.

EXAMPLE 1

Preparation of a System According to the Invention
2.0 g 17-β-estradiol semihydrate, micronised
60.0 g Cariflex® TR 1107 (styrene-isoprene-styrene block copolymer)
120.0 g staybelite ester 5E (thermoplastic ester resin of colophony derivatives)
20 g viscous paraffin
are stirred in a cylindrical glass vessel until a uniform suspension results, and subsequently coated at a gap width of 500 micrometers onto a 100-μm-thick polyester film precoated with 2 g/m² silicone rubber. The coating is dried at 25° C., 50° C., 80° C. and at 95° C. for 10 minutes at each temperature. Immediately, a 15-μm-thick polyester film is placed (laminated) under roll pressure onto the dried layer, avoiding air bubbles.

By punching with a wad punch, transdermal systems of 10 cm² are obtained, which are packed in composite packageing material of paper/aluminium foil/heat sealing layer, adding a drying tablet containing 0.3 g calcium sulfate (which has been previously predried at 180° C.).

Subsequently, 15-μm-thick polyester film is placed (laminated) onto the still warm layer under roll pressure, avoiding air bubbles.

By punching with a wad punch, transdermal systems of 20 cm² are obtained.

EXAMPLE 2

Comparison Example to 1
2.0 g 17-β-estradiol semihydrate, micronised
60.0 g Cariflex® TR 1107 (styrene-isoprene-styrene block copolymer)
120.0 g staybelite ester 5E (thermoplastic ester resin of colophony derivatives)
20 g viscous paraffin
are stirred at room temperature in a cylindrical glass vessel until a homogenous suspension is obtained, and subsequently coated at a gap width of 500 micrometers onto a 100-micrometer-thick polyester film (Scotchpak® 1022) which has been pre-coated with fluoropolymer. The spread is dried at 25° C., 50° C., 80° C. and at 95° C. for 10 minutes at each temperature. Immediately, a 15-μm-thick polyester film is placed (laminated) under roll pressure onto the dried layer, avoiding air bubbles.

By punching with a wad punch, transdermal systems of 10 cm² are obtained, which are packed in composite packageing material of paper/aluminium foil/heat sealing layer, adding a drying tablet containing 0.3 g calcium sulfate (which has been previously predried at 180° C.). Subsequently, 15-μm-thick polyester film is placed (laminated) under roll pressure onto the still warm layer, avoiding air bubbles.

By punching with a wad punch, transdermal systems of 20 cm² are obtained.

What is claimed is:

1. A transdermal therapeutic system having a layered structure, comprising:
   (1) a backing layer,
   (2) at least one matrix layer consisteng of base materials and containing at least one active substance, wherein at least one active substance is present in an oversaturated state, and
   (3) a removable protective layer coated with an abherent, said abherent having a lower diffusion coefficient than the diffusion coefficient of the base materials in the matrix layer.

2. The transdermal therapeutic system according to claim 1, wherein the diffusion coefficient of the abherent is at most one tenth of the diffusion coefficient of the base materials in the matrix layer.

3. The transdermal therapeutic system according to claim 1 wherein the abherent is a fluorinecontaining polymer.

4. The transdermal therapeutic system according to claim 1, wherein the abherent is coated onto the protective layer in a thickness of between 0.1 to 5 μm, as a continuous layer.

5. The transdermal therapeutic system according to claim 1 wherein the base materials of the matrix layer comprises water-insoluble, skin-compatible polymers and resin components suitable for skin contact.

6. The transdermal therapeutic system according to claim 5, wherein the polymers are copolymers of dienes, styrene, polyisobutylene or natural rubber.

7. The transdermal therapeutic system according to claim 5, wherein the resin components are derivatives of natural resins or hydrocarbon derivatives.

8. The transdermal therapeutic system according to any one of claims 2–7, wherein at least one active substance is a steroid hormone.

* * * * *